(12) United States Patent
Shoemaker

(10) Patent No.: US 7,794,985 B2
(45) Date of Patent: Sep. 14, 2010

(54) METHODS AND COMPOSITIONS FOR RAPID AMPLIFICATION, CAPTURE AND DETECTION OF NUCLEIC ACIDS AND PROTEINS

(75) Inventor: Daniel D. Shoemaker, San Diego, CA (US)

(73) Assignee: GHC Technologies, Inc., La Jolla, CA (US)

( * ) Notice: Subject to any disclaimer, the term of this patent is extended or adjusted under 35 U.S.C. 154(b) by 72 days.

(21) Appl. No.: 12/079,851

(22) Filed: Mar. 27, 2008

(65) Prior Publication Data
US 2009/0061435 A1 Mar. 5, 2009

Related U.S. Application Data

(60) Provisional application No. 60/921,796, filed on Apr. 4, 2007.

(51) Int. Cl.
*C12Q 1/68* (2006.01)
*C12P 19/34* (2006.01)

(52) U.S. Cl. .................... 435/91.2; 435/6; 435/91.1

(58) Field of Classification Search ................ None
See application file for complete search history.

(56) References Cited

U.S. PATENT DOCUMENTS

| | | | |
|---|---|---|---|
| 5,573,914 A * | 11/1996 | Love | 435/6 |
| 5,635,352 A * | 6/1997 | Urdea et al. | 435/6 |
| 2004/0203019 A1 | 10/2004 | Kurn | |
| 2004/0209298 A1 * | 10/2004 | Kamberov et al. | 435/6 |
| 2006/0078906 A1 | 4/2006 | Chen et al. | |
| 2007/0054301 A1 | 3/2007 | Becker et al. | |

OTHER PUBLICATIONS

Shoemaker, Daniel D, Quantitative Phenotypic Analysis of Yeast Deletion Mutants Using a Highly Parallel Molecular Bar-coding Strategy; Nature Genetics; Dec. 1996, pp. 450-456; V. 14; Nature Publishing Group; U.S.A.

* cited by examiner

*Primary Examiner*—Young J Kim
(74) *Attorney, Agent, or Firm*—Roeder & Broder LLP; James P. Broder

(57) ABSTRACT

A method for detecting the presence of a nucleic acid template (110) in a sample includes the steps of combining the sample in a reaction vessel with a first primer (112F) and a second primer (112R) having a first section (114), a second section (118) and a spacer (116). The method also includes one or more of the steps of extending the first section (114) with additional nucleotides, binding the first primer (112F) to the extended first section, extending the first primer (112F) with additional nucleotides and terminating extension of the first primer (112F) with the spacer (116). The first section (114) includes a plurality of nucleotides that bind with a portion of the nucleic acid template (110). The second section (118) is spaced-apart from the first section (114) and includes a plurality of nucleotides that do not bind with the nucleic acid template (110). The spacer (116) couples the first section (114) to the second section (118). The invention is also directed toward the second primer (112R).

20 Claims, 13 Drawing Sheets

Structure of SP26Ach spacer (within an oligonucleotide):

Structure of 2'-U-SUC, ethanol amine derivatized (within an oligonucleotide):

SEQUENCE LISTING

<160> NUMBER OF SEQ ID NOS: 4

<210> SEQ ID NO 1
<211> LENGTH: 11
<212> TYPE: DNA
<213> ORGANISM: Artificial
<220> FEATURE:
<223> OTHER INFORMATION: One embodiment of a DNA or RNA forward tapper.

<400> SEQUENCE: 1
atgaagaaga g                                                               11

<210> SEQ ID NO 2
<211> LENGTH: 44
<212> TYPE: DNA
<213> ORGANISM: Artificial
<220> FEATURE:
<223> OTHER INFORMATION: One embodiment of an extension-capture probe
      for capturing certain nucleic acid sequences.

<400> SEQUENCE: 2
ttcttctcgc aaatatagcc cccccgccct tttttttttt tttt                           44

<210> SEQ ID NO 3
<211> LENGTH: 22
<212> TYPE: DNA
<213> ORGANISM: Artificial
<220> FEATURE:
<223> OTHER INFORMATION: One embodiment of a strand of a denatured
      isothermal amplification amplicon that binds to an
      extension-capture probe.

<400> SEQUENCE: 3
atgaagaaga gcgtttatat cg                                                   22

<210> SEQ ID NO 4
<211> LENGTH: 47
<212> TYPE: DNA
<213> ORGANISM: Artificial
<220> FEATURE:
<223> OTHER INFORMATION: One embodiment of an extended extension-capture
      probe.

<400> SEQUENCE: 4
tacttcttct cgcaaatata gccccccgc ccttttttttt ttttttt                        47

METHODS AND COMPOSITIONS FOR RAPID AMPLIFICATION, CAPTURE AND DETECTION OF NUCLEIC ACIDS AND PROTEINS

REFERENCE TO RELATED APPLICATION

This application claims domestic priority on U.S. Provisional Application Ser. No. 60/921,796, filed on Apr. 4, 2007. The contents of U.S. Provisional Application Ser. Nos. 60/921,796 are incorporated herein by reference to the extent permitted.

BACKGROUND

Rapid nucleic acid amplification and detection has become increasingly more critical, such as in the areas of biodefense and Point of Care clinical diagnostics. However, efforts to decrease the time required for amplification and analysis of nucleic acid sequences and various proteins without sacrificing accuracy have not been altogether satisfactory. Although certain processes have been advanced in recent years such as using various isothermal amplification methods, many such methods have drawbacks that are challenging or impossible to overcome. These drawbacks can include difficult and/or slow initiation, limited site selection of primers on a DNA, RNA or protein template, sensitivity and specificity issues, difficulties with multiplexing and/or overall suboptimal performance levels. Further, conventional (non-isothermal) polymerase chain reaction (also commonly known as "PCR") based amplification methods can require extensive time to perform and can be limited by contamination issues.

Additionally, one drawback with certain isothermal amplification methods includes generating false reaction products (also referred to as "negative" reaction products). These negative products are the result of reactions involving forward and/or reverse primers (also sometimes referred to herein as "tappers") used during amplification, without regard for the presence or absence of the DNA, RNA or protein sought to be detected. In other words, over time, negative reaction products are synthesized which would appear to indicate the presence of a particular nucleic acid or protein, even though no such nucleic acid or protein is actually present. Unfortunately, the negative reaction products can be essentially very similar or even indistinguishable from the true "positive" reaction products that are generated when the DNA, RNA or protein sought to be detected is actually present. As a result, detection accuracy can be significantly compromised. It is also complicated to perform isothermal amplification reactions in a multiplexed format, thus limiting the utility of this type of detection strategy.

SUMMARY

The present invention is directed toward a method for detecting the presence of a nucleic acid template in a sample. In one embodiment, the method includes the step of combining the sample in a reaction vessel with a first primer and a second primer having a first section, a second section and a spacer. The method also includes one or more of the steps of extending the first section with additional nucleotides, binding the first primer to the extended first section, extending the first primer with additional nucleotides and terminating extension of the first primer with the spacer of the second primer. In one embodiment, the first section includes a plurality of nucleotides that bind with a portion of the nucleic acid template. The second section is spaced-apart from the first section. In certain embodiments, the second section includes a plurality of nucleotides that do not bind with the nucleic acid template. The spacer couples the first section to the second section.

In one embodiment, the spacer is devoid of nucleotides the second section includes at least approximately 5 nucleotides and less than approximately 50 nucleotides. In another embodiment, the second section includes at least approximately 20 nucleotides and less than approximately 30 nucleotides. In one embodiment, the second section includes a sequence of nucleotides that is non-complementary to the nucleic acid template. Further, the step of combining can include selecting a tag sequence to be included in the second section. In certain embodiments, the tag sequence can be based on one or more criteria that are not dependent upon any sequence of nucleotides in the nucleic acid template. In one embodiment, the tag sequence is specific to the nucleic acid template to be detected. The tag sequence can be formed from at least 1 and less than approximately 5 nucleotides.

The method can also include the step of adding a forward tapper and a reverse tapper to the reaction vessel. In one embodiment, the forward tapper can bind to the second section and extend along the second section. The method can also include the step of amplifying the second section to increase the number of second sections in the reaction vessel. In one embodiment, the step of amplifying occurs substantially isothermally.

The method can also include the step of selecting a tag sequence to be included in the second section. In some embodiments, the tag sequence can be based on one or more criteria that are not dependent upon any sequence of nucleotides in the nucleic acid template. Further, the step of the forward tapper binding can include the forward tapper binding to a portion of the second section that does not include the tag sequence. In one embodiment, the step of combining can include adding a plurality of second primers. In some embodiments, each of the second primers can include a different second section that is specific for detecting one particular nucleic acid template in the sample.

The present invention is also directed toward a second primer that interacts with a first primer during detection of the presence of a nucleic acid template in a sample. In one embodiment, the second primer includes a first section, a second section and a spacer. The first section includes a plurality of nucleotides. Further, the first section can be adapted to bind with a portion of the nucleic acid template and extend into an extended first section so that the first primer binds to the extended first section and extends. The second section is spaced-apart from the first section, and includes a plurality of nucleotides that are adapted not to bind with the nucleic acid template. The spacer couples the first section to the second section. In various embodiments, the spacer terminates extension of the first primer.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1A:
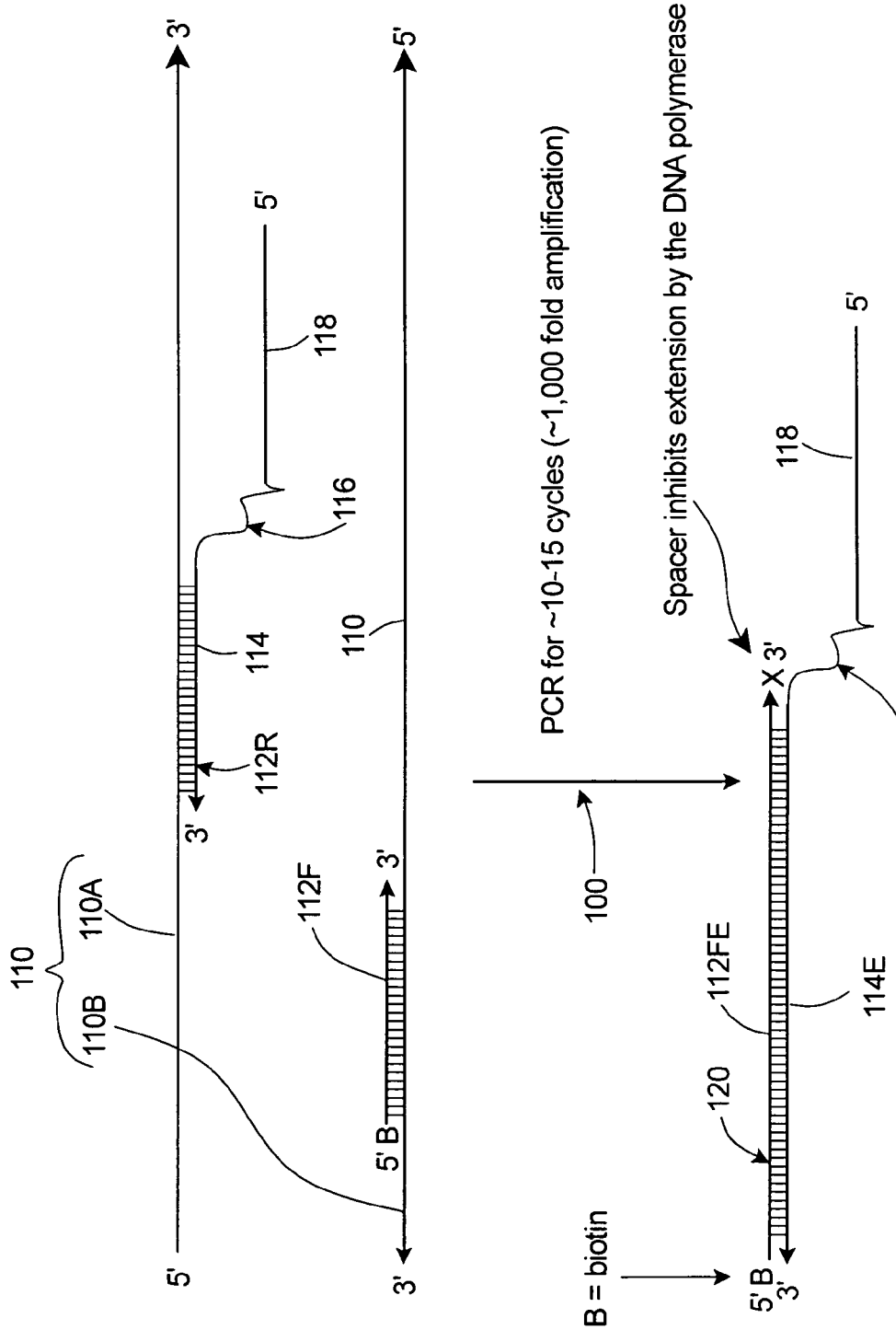
FIGS. 1A-1C are workflow diagrams showing one embodiment of a method for amplification and detection of nucleic acid sequences in accordance with the present invention.
Figure 1B:
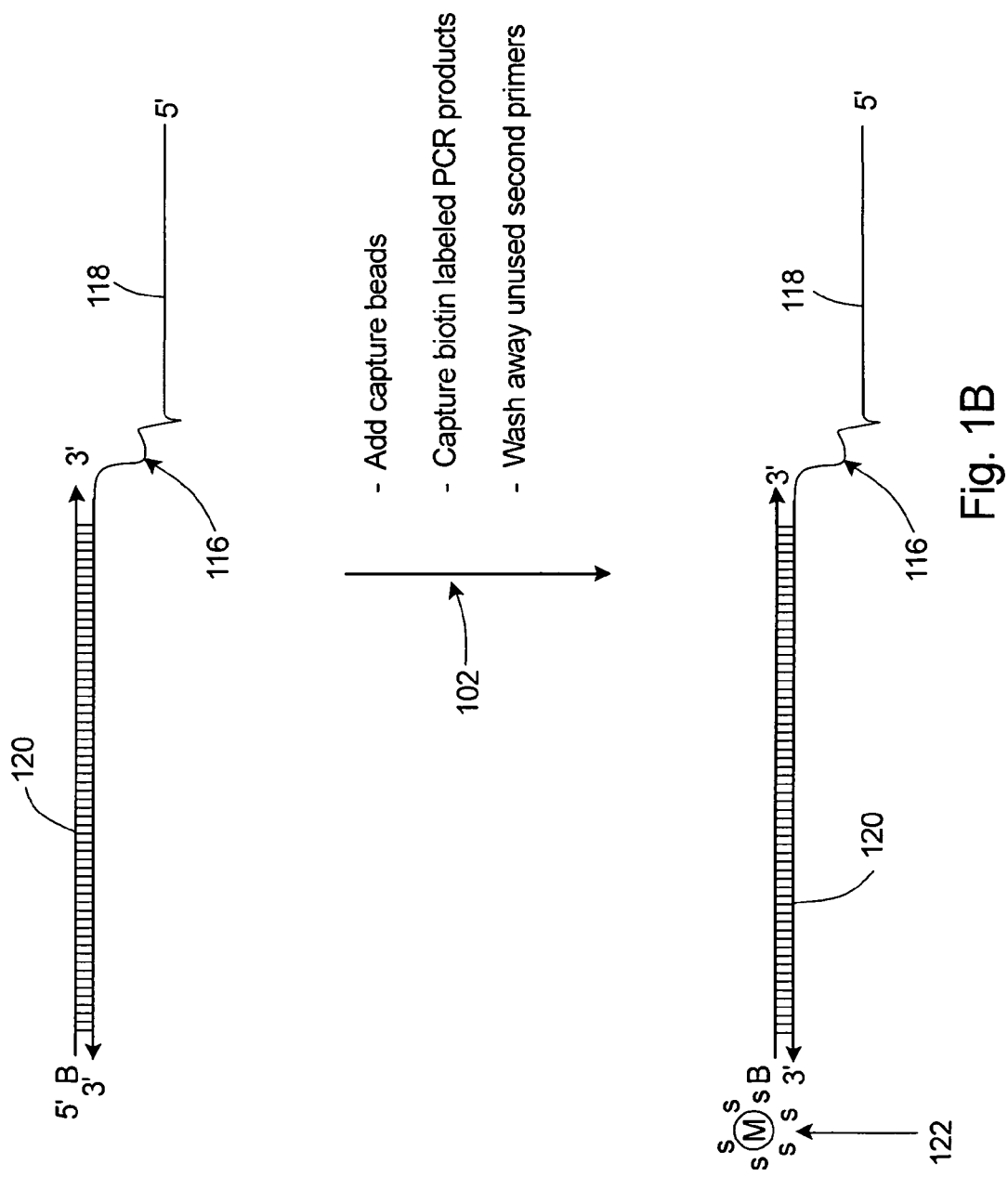
Figure 1C:
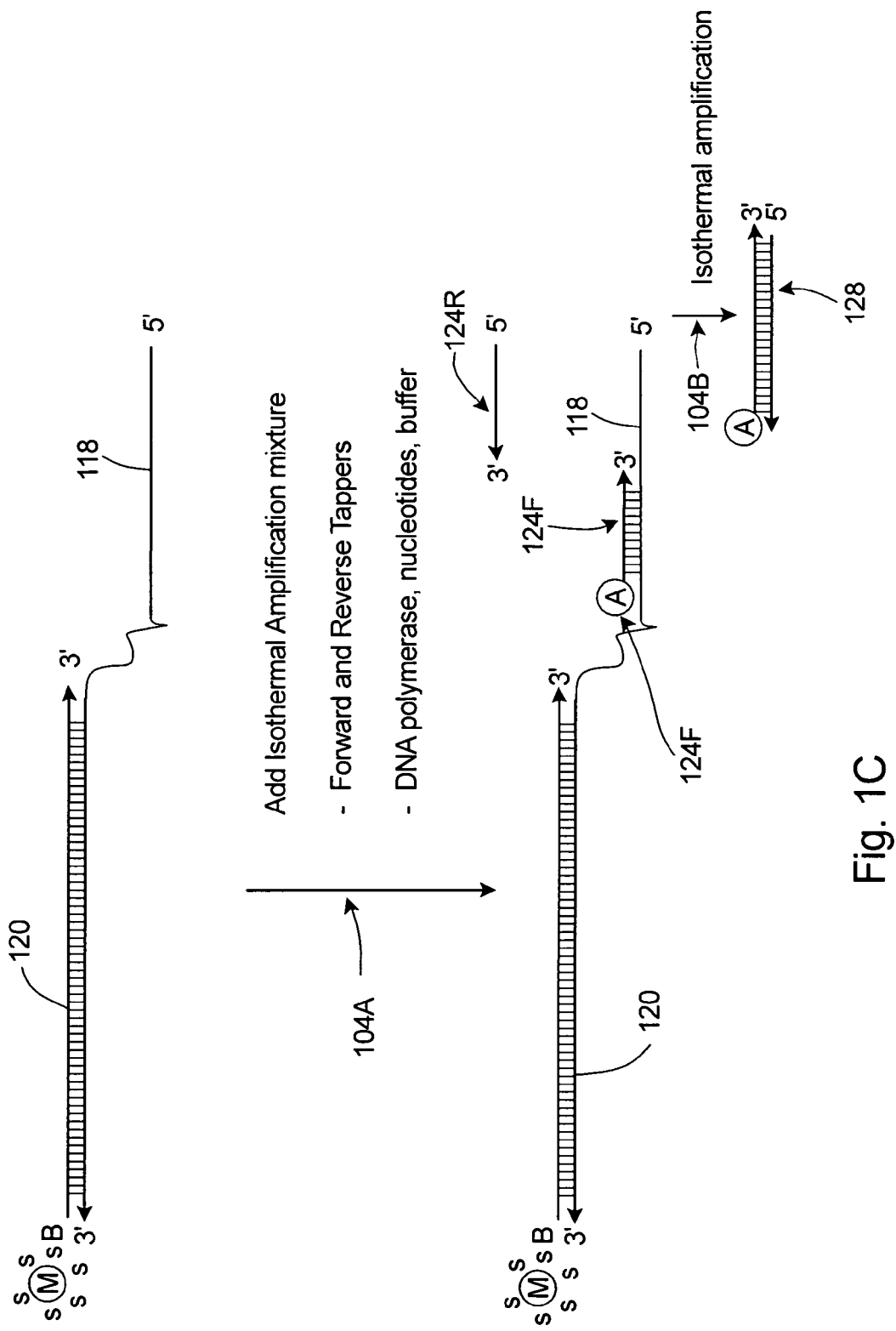

FIGS. 1A-1C are workflow diagrams showing one embodiment of a method for amplification and detection of nucleic acid sequences in accordance with the present invention. In the embodiment illustrated in FIG. 1A, at step 100, a genomic template 110 (also sometimes referred to herein simply as "template") having a first strand 110A and a second strand 110B, a polymerase (not shown), and a primer pair that includes a forward PCR primer 112F (also referred to herein as a "first primer") and a reverse PCR primer 112R (also referred to herein as a "second primer"), are introduced into a reaction vessel (not shown) for a plurality of polymerase chain reaction ("PCR") cycles. In FIG. 1A, the template 110 is shown as being denatured, although it is understood that during certain stages of PCR, the template 110 may not be denatured. The polymerase used can include any suitable polymerase known to those skilled in the art of PCR, such as Taq polymerase, as one non-exclusive example. The number of PCR cycles at step 100 can vary, but in certain embodiments, the number of PCR cycles is a reduced number relative to conventional PCR. For example, in one embodiment, the number of PCR cycles can be approximately 10-15 cycles, which can generate approximately a 1000-fold amplification. However, any suitable number of PCR cycles can be used to generate the desired extent of amplification at step 100.

In certain embodiments, each PCR cycle includes fluctuating the temperature within the reaction vessel through a plurality of different temperatures to cyclically raise and lower the temperature of the reagents within the reaction vessel. The specific temperatures to be achieved within the reaction vessel can vary depending upon the types of reagents used. For instance, in one representative, non-exclusive example of one PCR cycle, the temperature can start at approximately 94° C., is then lowered to approximately 55° C., and is then raised to approximately 72° C. In this example, at 94° C., the double-stranded template denatures. At 55° C., the primer anneals to the now single-stranded template. At 72° C., the polymerase extends the annealed primer(s). The temperatures described above are provided for one possible specific set of reagents for ease of understanding and are in no way intended to limit the scope of the present invention.

Further, in this embodiment, the target template 110 that is being detected can include DNA, RNA or any other suitable nucleic acid sequences. Alternatively, the template 110 can be any suitable protein molecule which may be useful or desirable to detect, as described in greater detail below.

In the embodiment illustrated in FIG. 1A, the first primer 112F can be a 25-base primer. In this embodiment, the first primer 112F can include or be attached to a biotin moiety (illustrated as "B" in FIG. 1A) or other suitable type of moiety for later capture by a capture bead 122 (illustrated in FIG. 1B), for example.

In alternative embodiments, the first primer 112F can include any suitable number of bases (also sometimes referred to herein as "nucleotides"), which may be greater than or fewer than 25 bases, depending upon the reaction conditions and/or desired results, for example. As used herein, any reference to a "25mer" or any other specific length primer or other structure having a particular number of bases or base pairs is so identified for ease of discussion only, and is not intended to limit the scope of the type or length of the primers (or other structures) to any specific number of bases or base pairs.

In this embodiment, the second primer 112R includes a first section 114 and a spacer 116 (illustrated as a curved line in FIG. 1A) that is linked to the first section 114. The first section 114 can include any suitable number of bases. In one non-exclusive embodiment, the first section 114 can include approximately 25 bases, although it is recognized that the actual number of bases included in the first section 114 can be greater or fewer than 25.

Additionally, in this embodiment, the second primer 112R includes a second section 118 (also sometimes referred to herein as a "tail") on the 5' end that is linked to the spacer 116 so that the spacer 116 is positioned substantially between the first section 114 and the tail 118. In this embodiment, the tail 118 on the 5' end of the second primer 112R is illustrated as a 22mer, although it is recognized that the tail 118 can include any suitable number of bases that may alternatively be greater than or fewer than 22 bases. For example, in non-exclusive alternative embodiments, the tail 118 can include at least approximately 5 and less than approximately 50 bases.

As illustrated in FIG. 1A, the spacer 116 of the second primer 112R acts as an extension terminator of the first primer 112F during the PCR reaction. The spacer 116 maintains the tail 118 in a single-stranded state throughout the PCR amplification process. As referred to herein, the terms "extend" and "extension" can mean utilizing a polymerase to add nucleotides to a shorter strand that is bound to a longer strand in order to form a lengthier double-stranded sequence. For example, the first section 114 of the second primer 112R extends in the 3' direction following binding of the first section 114 to the first strand 110A of the template 110. Once the first section extends (hereinafter referred to as an "extended first section 114E"), the extended first section 114E and the first strand 110A denature as part of the PCR cycle. The first primer 112F binds with the extended first section 114E, and the first primer 112F extends in the 3' direction (hereinafter referred to as an "extended first primer 112FE"), i.e. toward the spacer 116. However, once the extension of the first primer 112F in the 3' direction reaches the spacer 116, extension is effectively inhibited or terminated, as indicated by the "X" in FIG. 1A. As a result, the tail 118 of the second primer 112R remains single-stranded.

Figure 2:
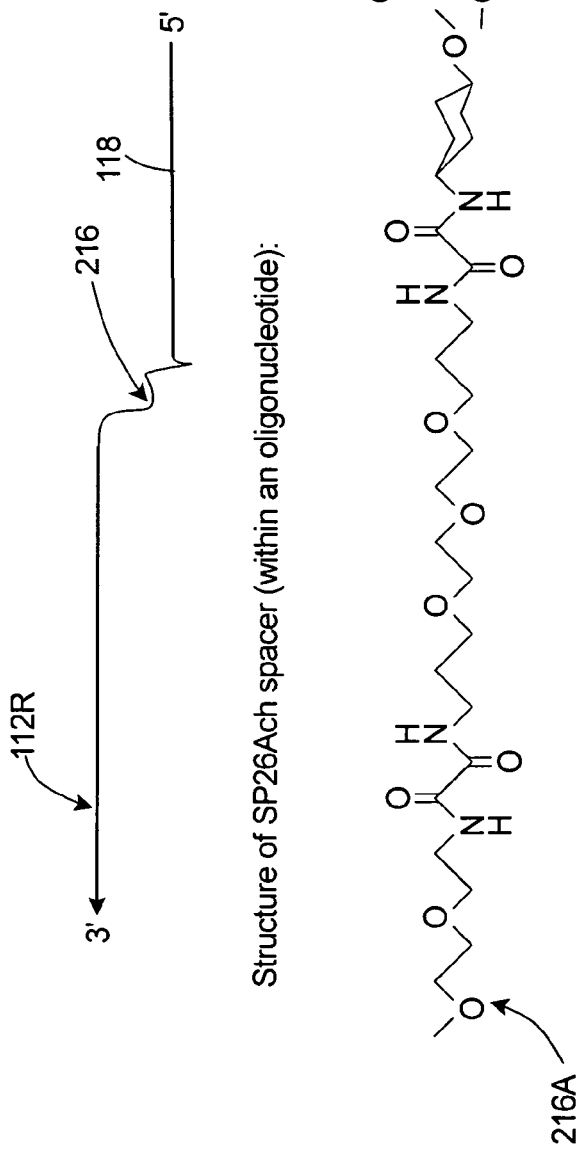
FIG. 2 is a structural diagram illustrating two non-exclusive representative examples of spacers that can be used in reverse PCR primers to generate PCR products containing desired single-stranded tails in accordance with the present invention.
Figure 2:
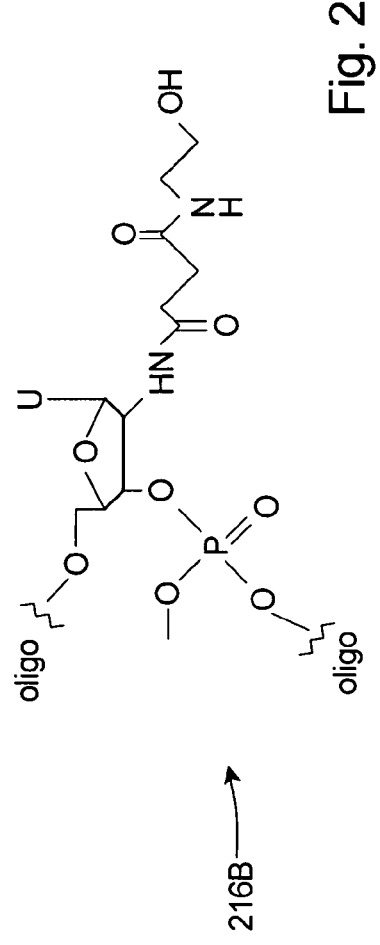

FIG. 2 illustrates two non-exclusive representative examples of spacers 216A, 216B that can be used in the second primers 112R (illustrated in FIG. 1A) to generate amplicons 120 (illustrated in FIG. 1A) each containing the desired single-stranded tail 118. The type of spacer 216 that can be used with the second primer 112R can vary widely. However, it is noted that these particular spacers 216A, 216B illustrated in FIG. 2 are provided for illustrative purposes only, and are not intended to limit the types of spacers 216 that can be used in the present invention. Basically, a suitable spacer 216 can include any molecular structure that inhibits extension of the first primer 112F (illustrated in FIG. 1A) so that the tail 118 on the 5' end of the second primer 112R remains single-stranded. In one embodiment, the spacer 216 does not include any bases. Alternatively, the spacer 216 can include one or more bases.

Referring back to FIG. 1A, the length and sequences of the first primer 112F and the second primer 112R can be selected to optimize the performance of the PCR amplification reaction. In one non-exclusive example, the length and sequences of the first primer 112F and the second primer 112R can be selected based on the length of a desired amplicon 120, such as an amplicon 120 having 60 base pairs as illustrated in FIG. 1A. By utilizing PCR methods known to those skilled in the art, specific primers 112F, 112R can be selected that anneal to particular locations on the target template 110 to yield an amplicon 120 having a desired length. It is recognized that the amplicon 120 can include any suitable number of base pairs, and that the example illustrated in FIG. 1A is provided as one representative embodiment for ease of understanding and explanation only.

In FIG. 1A, the first primer 112F and the first section 114 of the second primer 112R are specific to the nucleic acid sequence that is being detected. Thus, it may be necessary to include different first and second primers 112F, 112R in the reaction mixture if potential detection of more than one nucleic acid sequence is desired, such as in the case of multiplex PCR. For example, screening for a plurality of possible templates, i.e. different nucleic acid sequences, requires a plurality of different primer pairs 112F, 112R, each having the first primers 112F labeled with biotin and the second primers 112R with spacers 116 and tails 118 which serve as templates for an isothermal phase of the amplification reaction, as described in greater detail below.

In certain embodiments, the tail 118 that is linked to the spacer 116 in the second primer 112R can have any suitable sequence of bases. For example, in one embodiment, the sequence of bases that comprises the tail 118 is not based on the sequence of the template 110 that is being detected. Instead, the sequence of bases that form the tail 118 can be based on factors or other criteria that are known to increase performance, i.e. speed and accuracy, during isothermal reactions. Therefore, the specific types of bases and their sequence in the tail 118 are in no way limited or restricted by the type of target sequence of the template 110 that is being detected. In other words, the sequence of bases included in the tail 118 can be partially or completely non-complementary to the sequence of bases in the template 110 to be detected. In various embodiments, this is particularly useful where the specific target sequence is not favorable for rapid isothermal amplification.

Following PCR, which yields amplicons 120 such as that illustrated in FIG. 1B, a plurality of capture beads 122 can be added directly to the PCR mixture at step 102. The specific structure of the capture beads 122 can vary to suit the design requirements of the amplicon 120 to be captured. In one non-exclusive example, Streptavidin coated magnetic capture beads 122 having a diameter of approximately 1 micron, for example, can be used. The capture beads 122 capture the biotin labeled amplicons 120 which include the spacer 116 and the single-stranded tails 118, as illustrated in FIG. 1B. Step 102 can also include a washing phase during which the captured amplicons 120 remain bound to the capture beads 122 while the unused second primers 112R, the polymerase and the DNA or RNA templates 110 are washed away.

At step 104 in FIG. 1C, an isothermal amplification ("ITA") reaction is performed. At sub-step 104A, the capture beads 122 containing the amplicons 120 are resuspended in a mixture containing a forward ITA primer 124F (also sometimes referred to herein as a forward tapper 124F) and a reverse ITA primer 124R (also sometimes referred to herein as a reverse tapper 124R), a second polymerase (not shown in FIG. 1C) and nucleotides (not shown in FIG. 1C). In the non-exclusive embodiment illustrated in FIG. 1C, the tappers 124F, 124R can have 11 bases. Alternatively, the tappers 124F, 124R can have greater or fewer than 11 bases. The forward tapper 124F includes a fluorescent label 126 such as an Alexa dye (illustrated as an "A" in FIG. 1C). The sequence of the 11-base forward tapper 124F is complementary to the first 11 bases on the tail 118. The reverse tapper 124R does not include the fluorescent label 126. In this embodiment, the reverse tapper 124R is substantially similar or identical to the last 11 bases on the tail 118.

During sub-step 104B, the isothermal amplification reaction occurs. The temperature of this reaction is determined depending upon the melting temperature ($T_m$) of the product from the isothermal amplification. For example, in the embodiment illustrated in FIG. 1C, isothermal amplification can be expected to generate a plurality of fluorescently-labeled, 22 base pair ITA amplicons 128. The temperature of the isothermal amplification reaction is selected such that denaturing, annealing and extending can readily occur at a single reaction temperature. In one embodiment, for example, the temperature of the isothermal reaction can be held substantially constant at approximately 65° C., although it is recognized that this temperature can be varied to suit the requirements of the specific reactants and other reaction conditions.

In this embodiment, because the single-stranded 5' tails 118 extend from the one end of the captured amplicons 120, the tails 118 are exposed allowing the tails 118 to react with the forward tapper 124F, without requiring that the amplicons 120 become denatured. In certain embodiments, the extension product (such as a 22mer) of the forward tapper 124F denatures from the tail 118 and becomes a template for the reverse tapper 124R, ultimately resulting in an exponential isothermal amplification.

Figure 3:
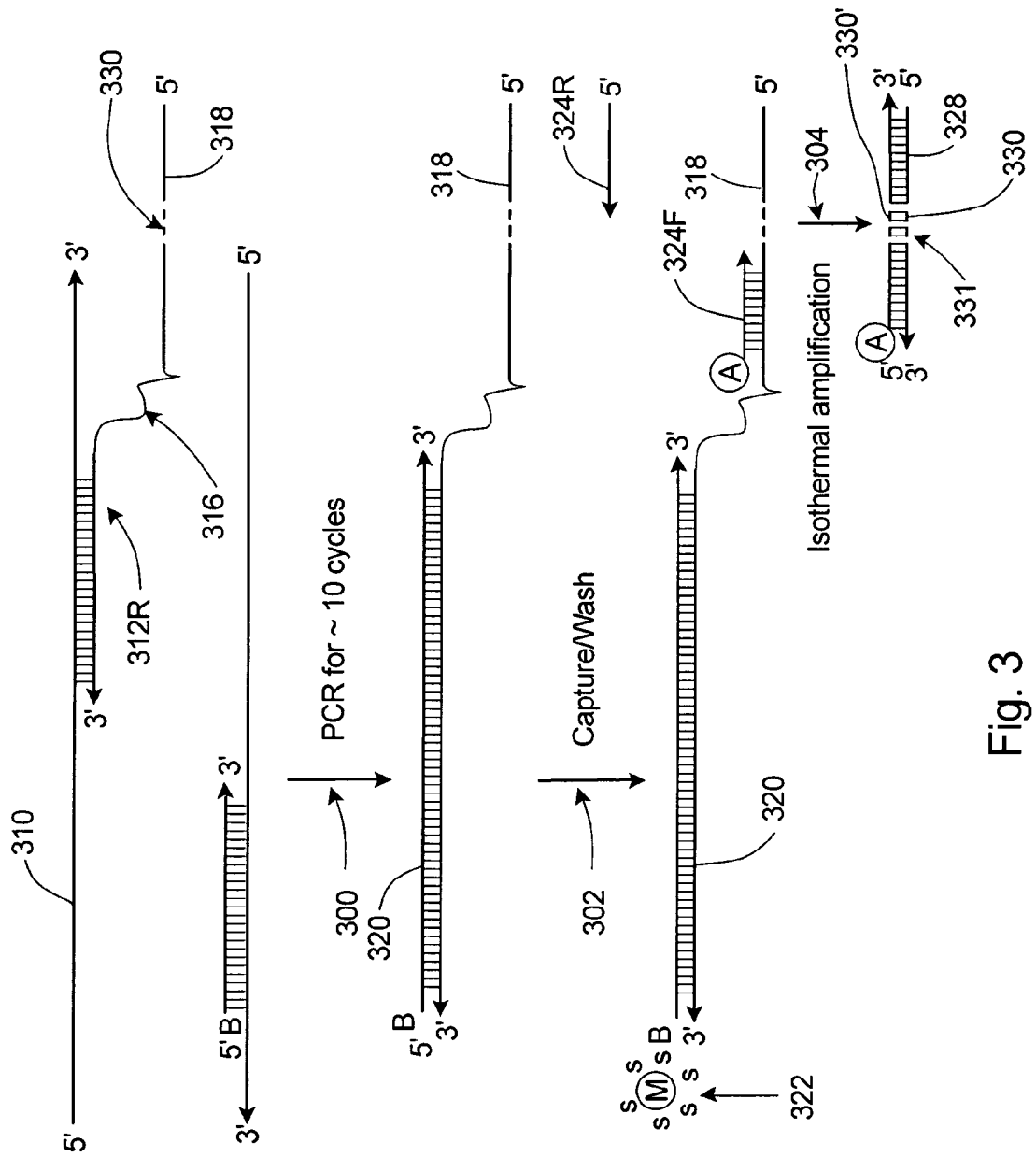
FIG. 3 describes a version of the invention which uses short tag sequences in the tails on a 5' end of the reverse PCR primers to facilitate multiplex amplification reactions.

FIG. 3 describes one embodiment of the invention which uses a short tag sequence 330 embedded within the single-stranded tail 318 of the second primer 312R to facilitate multiplex ITA reactions. As described above, the tail 318 can have any suitable length. For example, the tail 318 can include 26 bases. Alternatively, the tail 318 can include fewer than or greater than 26 bases.

In this embodiment, the tail 318 can be slightly different for each type of second primer 312R that is used in the reaction vessel. For example, each different type of tail 318 is identical to one another with the exception of a predetermined number of consecutive bases at or near the middle of the base sequence of the tail 318. In one such example, each different tail 318 can include a unique tag sequence 330 of approximately four bases (also sometimes simply referred to herein as a "tag") that enables the present invention to multiplex. As used herein, the term multiplex means the ability of the system to capture and detect one or more of a plurality of different nucleic acid sequences within the same reaction vessel.

The sequence of bases that comprises the tag 330 is not based on the template 110 having a target sequence that is being detected. Instead, the sequence of bases that form the tag 330 can be based on factors or other criteria that are known to increase performance, i.e. speed and accuracy, during isothermal reactions. Therefore, the specific types of bases and their sequence in the tag 330 are in no way limited or restricted by the type of target sequence of the template 110 that is being detected. In other words, the sequence of bases included in the tag 330 can be partially or completely non-complementary to the sequence of bases in the template 110 to be detected. Thus, in various embodiments, the tag 330 can allow discrimination of the different ITA products following a multiplexed ITA reaction.

Figure 4:
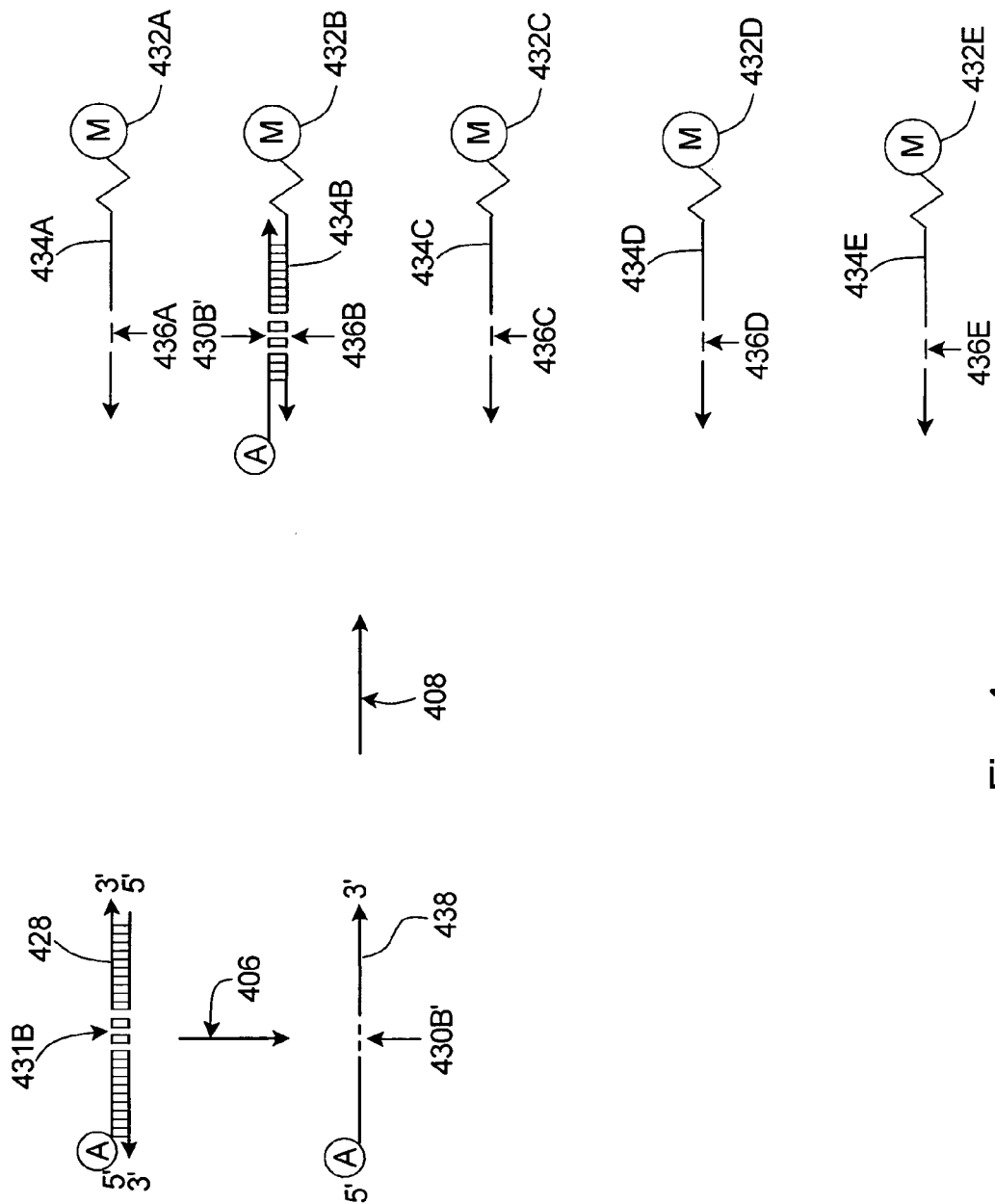
FIG. 4 illustrates a 5-plex bead-based detection scheme of a hybrid amplification strategy using 4 base pair (4 bp) tags.

The number of bases and composition of bases that form the tag 330 can vary. Although the tag 330 can include four bases as illustrated in FIG. 4, the tag 330 can alternatively include fewer than or greater than four bases. For example, the tag 330 can include from 1 to 5 or more bases. A tag 330 that includes two bases provides $4^2=16$ possible base combinations (based on four different possible bases including A, T, G and C, for example). A tag 330 that includes three bases provides $4^3=64$ possible base combinations. A tag 330 that includes four bases provides $4^4=256$ possible base combinations. As provided herein, each different combination is indicative of one specific sequence in order to accurately identify the nucleic acid or protein template 310.

At step 300, PCR is carried out to generate an amplicon 320 including the spacer 316 and the tail 318. In one such embodiment, PCR proceeds somewhat similarly as described previously herein, as illustrated in FIG. 3. The amplicon 320 can include any suitable number of base pairs.

At step 302, the amplicons 320 are captured with capture beads 322 as previously described, and the unused second primers 312R are washed away.

At step 304, forward tappers 324F and reverse tappers 324R are added, and isothermal amplification proceeds in a manner somewhat similar to that previously described. In this embodiment, the reaction product of isothermal amplification is an ITA amplicon 328 having a similar or identical number of base pairs as the number of bases in the tail 318. Further, the ITA amplicon 328 includes a double stranded tag 331 that includes the original tag 330 on one of the strands of the ITA amplicon 328, and a complementary tag 330' opposite the original tag 330 on the other strand of the ITA amplicon 328.

FIG. 4 illustrates one embodiment of a 5-plex bead-based scheme for detecting ITA products using tags 330 having four base pairs (4 bp). In certain embodiments, during or following the isothermal amplification step (step 304 in FIG. 3), a second type of magnetic capture bead 432A-E can be added to the reaction mixture. In one embodiment, one or more different types of intensity-encoded magnetic capture beads 432A-E are included in the isothermal amplification reaction. Each of the five different types of magnetic beads 432A-E can contain a different amount of an "encoding" fluorescent dye which can be detected using a different channel of a fluorescent microscope relative to the channel that is used to detect the fluorescently labeled isothermal amplification products. The specific strategy that can be used to generate a 5-plex set of spectrally encoded magnetic beads 432A-E can vary.

In one embodiment, each of the five types of magnetic capture beads 432A-E can contain a different locking nucleic acid (LNA) sequence capture probe 434A-E which is designed to capture the different types of isothermal amplification products. In one embodiment, the capture probes 434A-E can include approximately 19 bases. In non-exclusive alternative embodiments, the capture probes 434A-E can include greater than or fewer than 19 bases, as required. In still other embodiments, some or all of the nucleic acids in the sequence may not include locking nucleic acids. One example of a more detailed explanation of LNA's can be found in publications known to those skilled in the art, including, but not limited to "Locked Nucleic Acids (LNA) (Ørum, H., Jakobsen, M. H., Koch, T., Vuust, J. and Borre, M. B. (1999) Detection of the Factor V Leiden Mutation by Direct Allele-specific Hybridization of PCR Amplicons to Photoimmobilized Locked Nucleic Acids. Clin Chem., 45:1898-1905)", the publication of which is incorporated herein by reference to the extent permitted.

As provided herein, the capture beads 432A-E can be present during ITA. The ITA amplicon 428 including a double stranded tag 431 denatures (at step 406) because the reaction temperature is set above the $T_m$ of the ITA amplicon 428. The denatured strand 438 including the fluorescent label (indicated as an "A" within a circle in FIG. 4) can be captured (at step 408) by the capture probe 434A-E that is attached to a corresponding capture bead 432A-E. In one embodiment, the capture probe 434A-E has a melting temperature of approximately 70° C., allowing capture of the 22 base pair ITA product at the 65° C. reaction temperature in this example. In the embodiment illustrated in FIG. 4, the denatured strand having the Alexa dye marker includes the tag 430B', which is complementary to the original tag, e.g., 330 (illustrated in FIG. 3).

The number and types of capture beads 432A-E can vary depending upon the specific sequences sought to be monitored and/or detected by the system. For example, if five different genomic sequences are to be monitored and detected by the system, the capture beads 432A-E can each include one of five different 19mer (or some other length) capture probes 434A-E. In one embodiment, the five different capture probes 434A-E would be substantially identical, with the exception of four of the 19 bases, which would essentially be identical to one of the four-base tags 330 (illustrated in FIG. 3, for example) for each nucleic acid sequence to be monitored and/or detected. In other words, the sequences of the five different capture probes 434A-E are created to correspond to the tag sequences (430B') in the five different types of Alexa labeled 22mer ITA products.

For instance, if the four-base tag 330 on the original tail 318 for a *Y. pestis* PCR product is CCAG, a corresponding four-base (or other length) identifier 436A-E, e.g., 436B in FIG. 4, on one of the capture probes would also include bases CCAG. In one embodiment, this four-base identifier 436B is complementary to the tag 430B' on the strand 438 of the denatured ITA amplicon 428. Further, if the four-base tag on the original tail 318 for a *B. anthracis* PCR product is TTGC, the four-base identifier of one of the capture probes e.g., 434C, would also include bases TTGC, and so on. As a result, depending upon the specific ITA amplicon 428 that was amplified, only one specific type of capture probe 434A-E would capture the Alexa dye-bound strand 438. Using methods known to those skilled in the art, the magnetic capture bead 432A-E that is linked to this specific capture probe 434A-E can be identified, thereby detecting and identifying the original nucleic acid template 310 (illustrated in FIG. 3).

In an alternative embodiment, the capture probes 434A-E are utilized by themselves, with the magnetic capture beads 432A-E being omitted. In this embodiment, detection of the specific capture probes 434A-E can be accomplished in ways known to those skilled in the art of detection, without the use of the magnetic beads 432A-E. In an alternative embodiment, non-magnetic beads can also be used where the washing steps are performed using centrifugation or filtering instead of magnetic separation, for example.

Thus, it is the unique four-base (or other length) tag 330, rather than the tappers 324F, 324R, that determines the presence or absence of a particular nucleic acid sequence or protein. As a result, only one set of tappers 324F, 324R needs to be included in the reaction mixture during the isothermal amplification step. Therefore, a lower overall concentration of tappers 324F, 324R within the reaction mixture can be used because numerous different tappers, each requiring a minimum threshold concentration, are unnecessary. With this design, the isothermal amplification process is simplified and expedited. In certain alternative embodiments, a single common forward tapper 324F can be used with different types of reverse tappers 324R. This reduces the overall number of tappers 324F, 324R required for multiplexing which providing substantial sequence differences in the resulting isothermal amplification products to facilitate bead-based discrimination of the different threats. Still alternatively, a single common reverse tapper 324R can be used with different types of forward tappers 324F.

Figure 5:
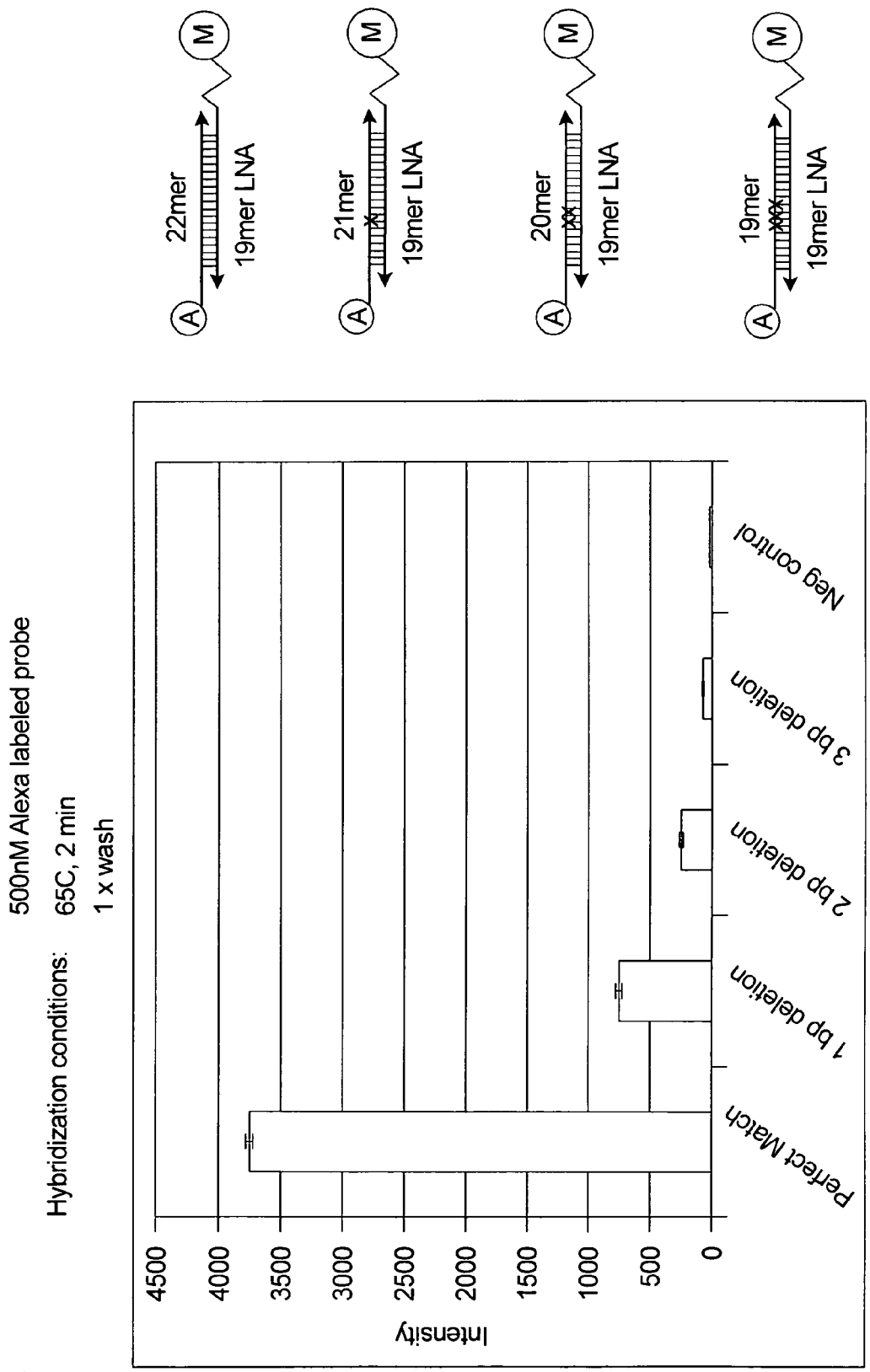
FIG. 5 is a graph of intensity as a function of base-pair deletions, illustrating discrimination between isothermal amplification products containing small numbers of deletions with a bead-based assay using LNA capture probes.

FIG. 5 is a bar graph that demonstrates that a bead-based assay using LNA capture probes can discriminate between isothermal amplification products containing small numbers of deletions. The graph in FIG. 5 illustrates that a greater number of mismatches between the reaction product and the capture probe results in a decrease in the signal intensity on the corresponding magnetic beads. A decreased magnetic bead signal signifies that fewer capture events of the mismatched reaction product actually occurred. For example, in one embodiment, a "perfect match" of a 22mer reaction product with the capture probe results in a signal intensity of approximately 3,800 units. With one deletion, such as a 21mer reaction product with the same capture probe, the signal intensity falls to approximately 750 units. With two bases deleted, the signal intensity drops to about 300 units. With three bases deleted, the signal intensity drops to about 100 units, just slightly more than the control with no nucleic acid template included in the reaction. Therefore, this multiplexed bead-based assay can distinguish between the different types of isothermal amplification products based on the different tags utilized.

Figure 6:
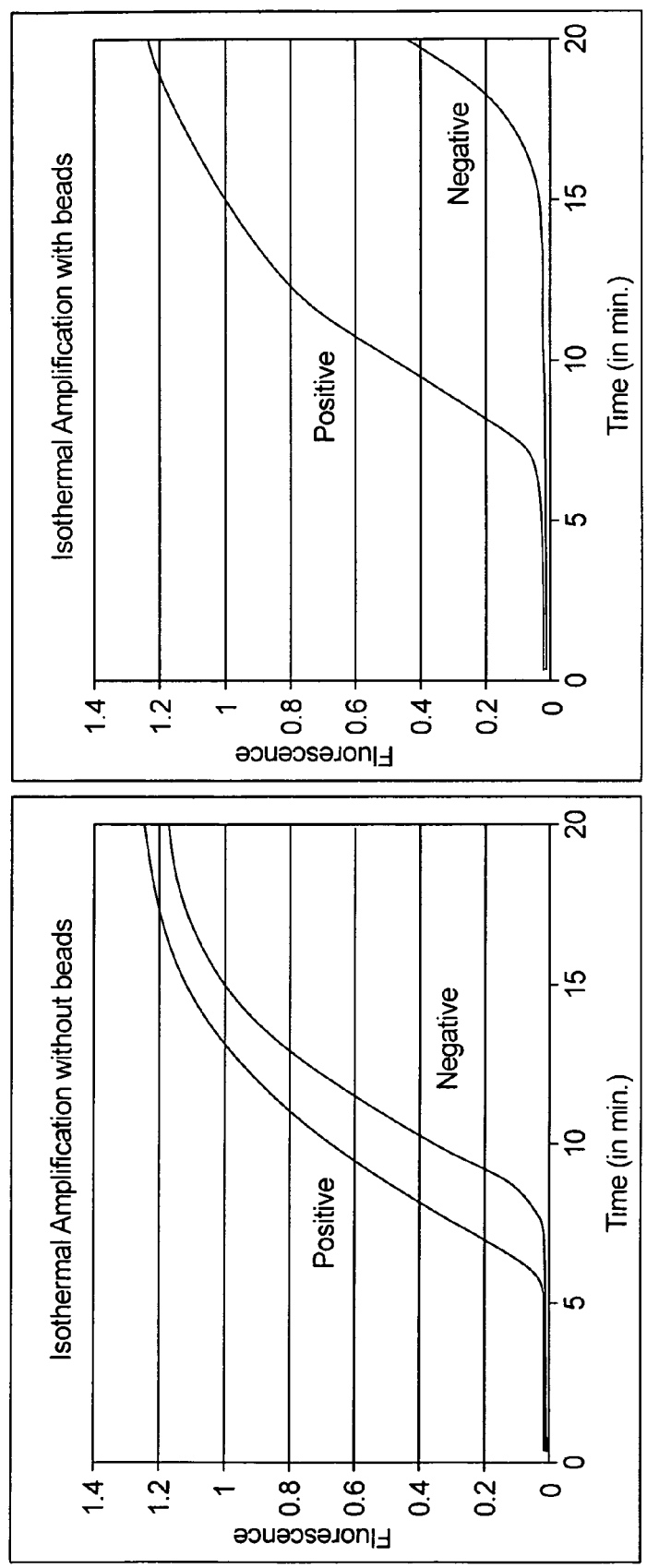
FIG. 6 shows two graphs of fluorescence as a function of time, with and without magnetic capture beads in the isothermal amplification reaction.

FIG. 6 shows two graphs which illustrate one or more advantages of including the magnetic capture beads in an isothermal amplification reaction. As indicated above, one of the drawbacks of certain isothermal amplification reactions is creation of negative reaction products. These negative reaction products have been found to be the result of the forward and reverse tappers combining with one another to varying degrees in a template-independent fashion. Although the precise mechanism for generation of this negative reaction product is not fully known, it is understood that certain reactions involving the tappers in a forward-forward, forward-reverse or reverse-reverse configuration occurs, which generate reaction products that can interfere with the accuracy of the detection process.

In certain embodiments, by including the magnetic capture beads in the reaction mixture during isothermal amplification, generation of the negative reaction products is inhibited. The graph on the left side of FIG. 6 illustrates an isothermal amplification where the capture beads were not included in the reaction mixture. In this isothermal amplification reaction, the generation of the undesirable negative reaction product(s) occurs relatively close in time to generation of the desirable positive reaction product. It is therefore difficult to accurately discriminate between the positive and negative reaction products.

However, in the graph on the right side of FIG. 6, the capture beads were included in the isothermal amplification reaction, which inhibited and/or delayed the negative reaction. Because of this greater time separation between generation of the positive and negative reaction products, the reaction can be strategically terminated prior to generation of any significant amount of negative reaction products, with little or no loss of generation of the positive reaction product. Consequently, the accuracy of detection of the actual presence of one or more nucleic acid sequences is enhanced.

One potential advantage of introducing tags into the isothermal amplification products is that positive reaction products have different sequences compared with the negative reaction products. For example, the negative reaction products typically contain the sequences of the tappers (forward-forward, forward-reverse or reverse-reverse) and do not contain the tag sequence which is only introduced via the template. Thus the positive reaction products contain a sequence that includes four extra base pairs (or some other suitable number depending on the tag size) in the amplification product which are relatively easy to detect using the appropriately designed capture beads. Any negative reaction product will be missing the four bases corresponding to the tag which are only introduced via the template. Therefore, the sequence of bases will not match the base sequence of the capture probes in a complimentary manner.

In an alternative embodiment, capture probes that are specific to the negative reaction product(s) can be utilized to effectively suppress proliferation of the negative reaction products. These capture probes that target the negative reaction products are also referred to herein as "suppression probes". The suppression probes can be added either during or after the isothermal amplification process. In certain embodiments, the positive reaction products will include the tag previously described, while the negative reaction products will not include this tag. Therefore, one or more different suppression probes can be used to specifically target and capture the different negative reaction products that may be formed during isothermal amplification before these negative reaction products can exponentially amplify. With this design, a smaller amount of negative reaction product will be generated, thus yielding a more accurate detection of the actual nucleic acid sequences present.

Figure 7:
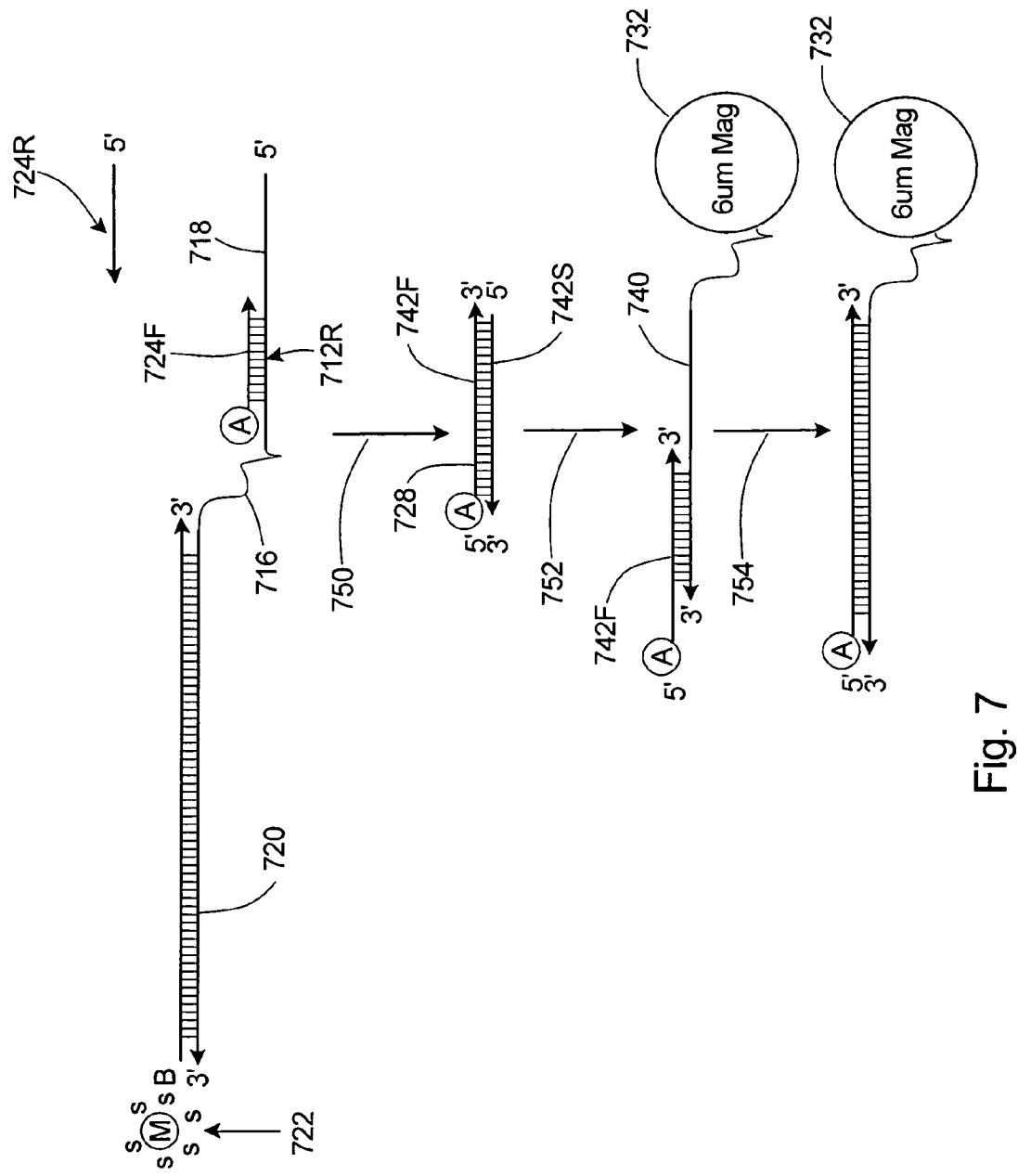
FIG. 7 is a workflow diagram showing a portion of another embodiment of a method of extension-capture including steps for amplification and detection of nucleic acid sequences in accordance with the present invention.

FIG. 7 is a workflow diagram showing a portion of another embodiment of a method including steps for amplification and detection of nucleic acid sequences in accordance with the present invention. In the embodiment illustrated in FIG. 7, the steps of PCR previously described to generate the amplicon 720 have been omitted for clarity. In this embodiment, the second primer 712R includes a spacer 716 and a tail 718 with no tag.

At step 750, forward tappers 724F and reverse tappers 724R are added to the reaction vessel to generate an ITA amplicon 728 during isothermal amplification as previously described.

At step 752, the ITA amplicon 728 denatures into a first strand 742F that includes an Alexa dye marker and a second strand 742S that does not include the Alexa dye marker. One or more spectrally encoded magnetic beads 732 containing extension-capture probes 740 are included either during or following the isothermal amplification reaction. In the embodiment illustrated in FIG. 7, the magnetic bead 732 is shown as a 6 micron diameter bead. However, it is recognized that the magnetic bead 732 can have any suitable diameter or shape, and that no limitations are intended by providing this particular example.

At step 754, the extension-capture probes 740 are designed so that the fluorescently labeled first strand 742F can bind to the extension-capture probe 740 and be extended by a polymerase in a direction toward the magnetic bead 732. Further, the extension-capture probe 740 is also extended by the polymerase in the 3' direction, i.e. toward the 5' end of the first strand 742F. Once extended, the resulting first strand 742F remains bound to the extended extension-capture probe 740, and thus, the magnetic bead 732, because of its greater length and greater resultant binding energy. In contrast, the non-extended 22 base amplification products and the tappers 724F, 724R do not bind to the extension-capture probe 740 under the stringent reaction conditions. This extension-capture strategy offers increased sensitivity and specificity relative to standard bead-based capture assays. The extension-capture probes 740 can be attached to any suitable type of surface, i.e. beads, microarrays or gel matrix, as non-exclusive examples.

As previously described, the tails 718 that are attached to the 5' ends of the second primers 712R can be specific to the particular templates 110 (illustrated in FIG. 1), i.e. nucleic acid sequences, to be monitored and/or detected. Importantly, the tails 718 of the second primers 712R can be selected based on performance qualities for the isothermal amplification/capture reactions rather than the sequence of the template 110 that is being detected. These performance qualities can include speed of the isothermal amplification reaction and the affinity for the complimentary capture probe, as non-exclusive examples. The extension-capture probes are likewise specific to the ITA amplicons 728 so that accurate detection of specific nucleic acids can occur. Any suitable number of different extension-capture probes 740 can be utilized during this process to allow assay multiplexing.

Figure 8:
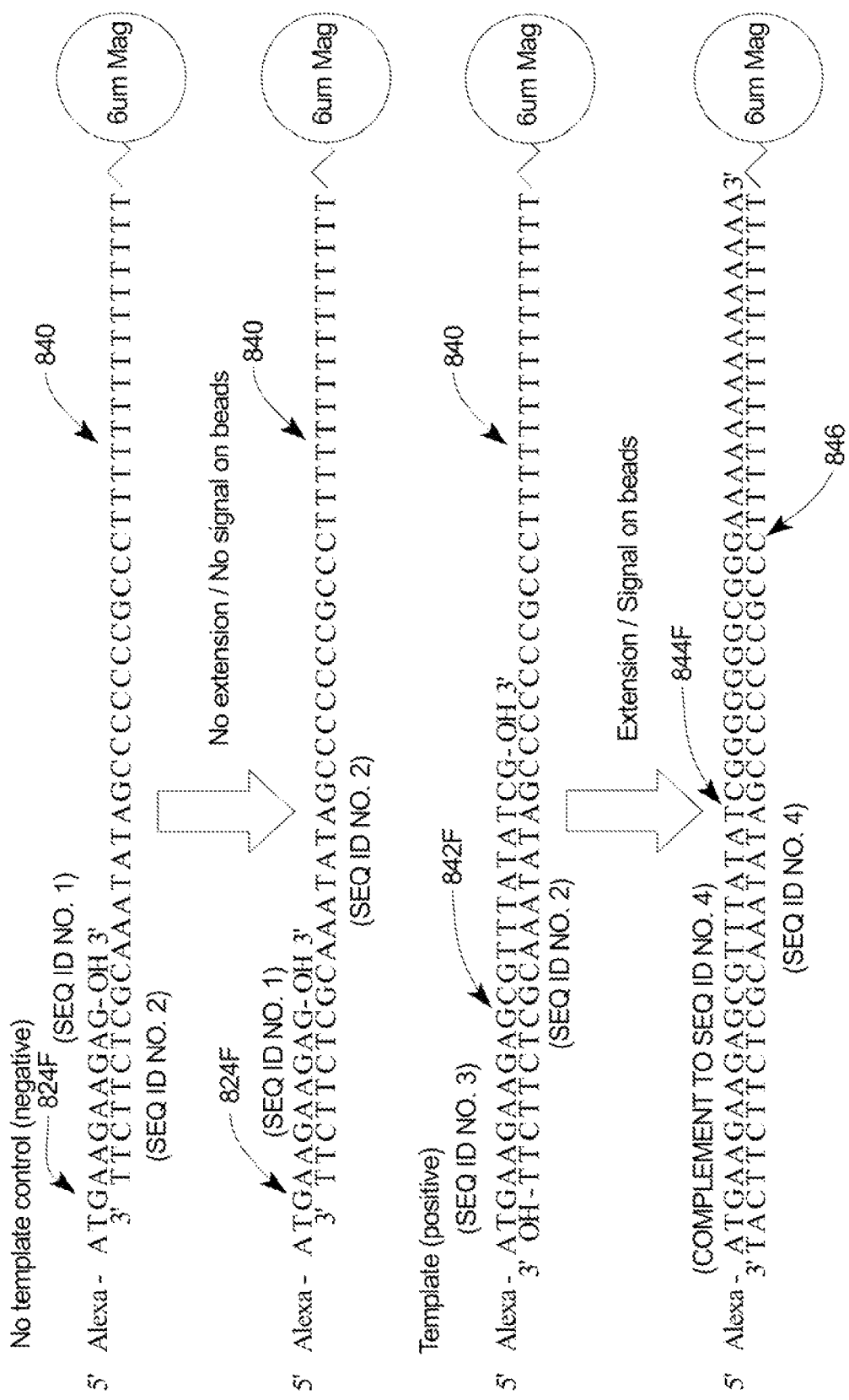
FIG. 8 illustrates one non-exclusive, representative example of how the extension-capture embodiment of the invention described in FIG. 7 is used to detect isothermal amplification reaction products.

FIG. 8 illustrates one non-exclusive, representative example of how the extension-capture embodiment of the invention described in FIG. 7 can be used to detect isothermal amplification reaction products from the ITA amplicon 728. In the event a forward tapper 824F binds to the extension-capture probe 840, the binding energy is low enough and the reaction temperature is high enough so that the forward tapper 824F will either not bind with the extension-capture probe 840, or if binding does occur, it will almost instantaneously denature from the extension-capture probe 840 prior to any significant extension occurring, as illustrated in the upper section of FIG. 8. Therefore, there is little or no false bead signal caused by binding and extension of the forward tapper 824F on the extension-capture probe 840. In contrast, when the first strand 842F of the denatured ITA amplicon 728 (illustrated in FIG. 7) binds to the extension-capture probe 840, sufficient homology exists to cause a greater level of binding energy, as illustrated in the lower section of FIG. 8. This increased binding energy allows extension to occur to generate an extended first strand 842FE and/or an extended extension-capture probe 846, ultimately generating a bead signal that can be readily detected by methods known to those skilled in the art.

Additionally, the extension-capture probes 840 can be specifically designed to have little or no overlap between the bases on the extension-capture probe 840 and the bases of the forward tapper 824F attached to the Alexa fluorescent dye. In general, the less overlap that is present, the lower the binding energy between the forward tapper 824F and the extension-capture probe 840.

Figure 9:
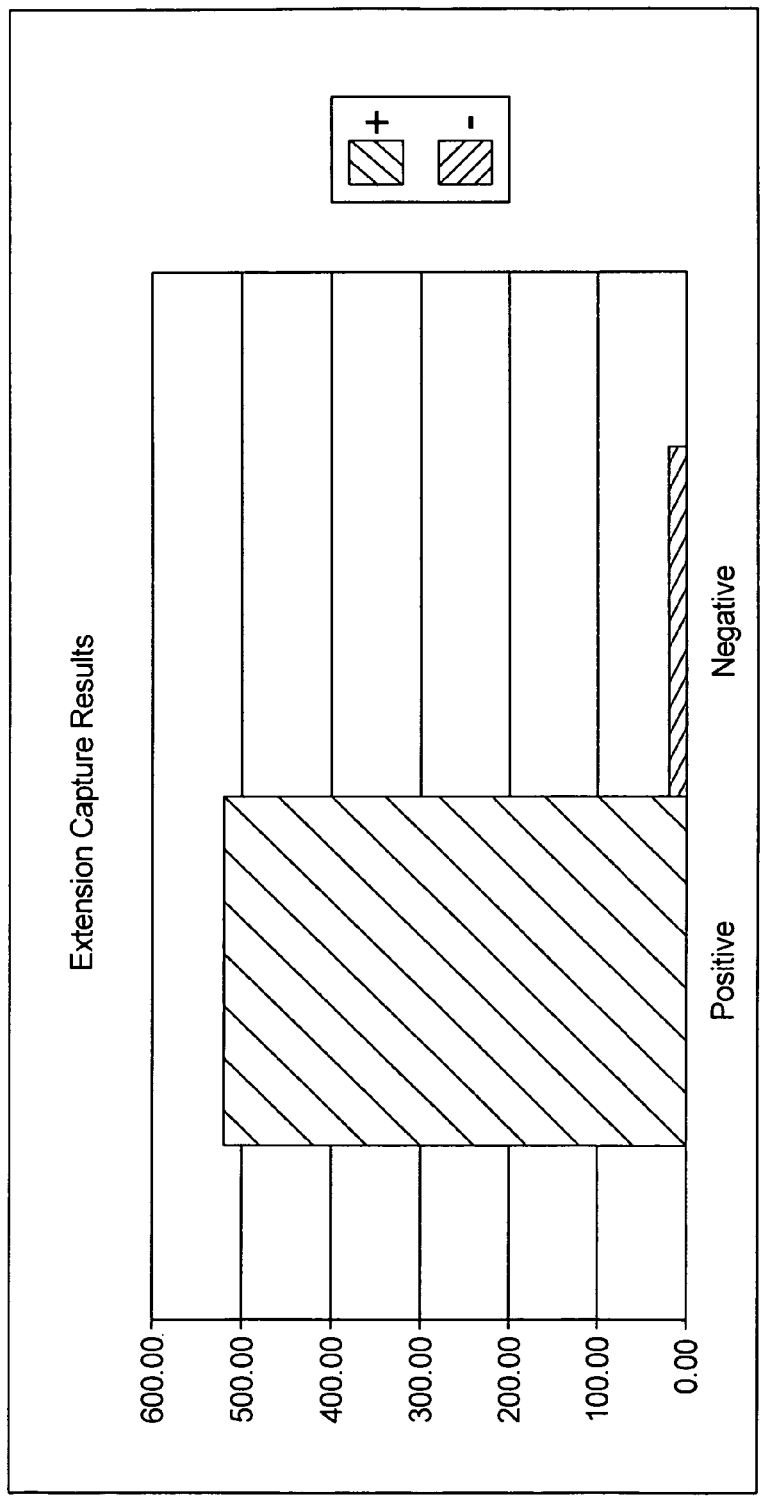
FIG. 9 is a bar graph of experimental results utilizing the extension-capture method.

FIG. 9 is a graph of experimental results utilizing the extension-capture method described previously. In this experiment, isothermal amplification reactions were performed both with and without a template 110 (illustrated in FIG. 1A) present. With the template 110 present (as indicated by the "positive"), a very high degree of the signal was detected on the magnetic beads as compared to when no template 110 was present (indicated by the "negative") and almost no detection occurred.

Figure 10:
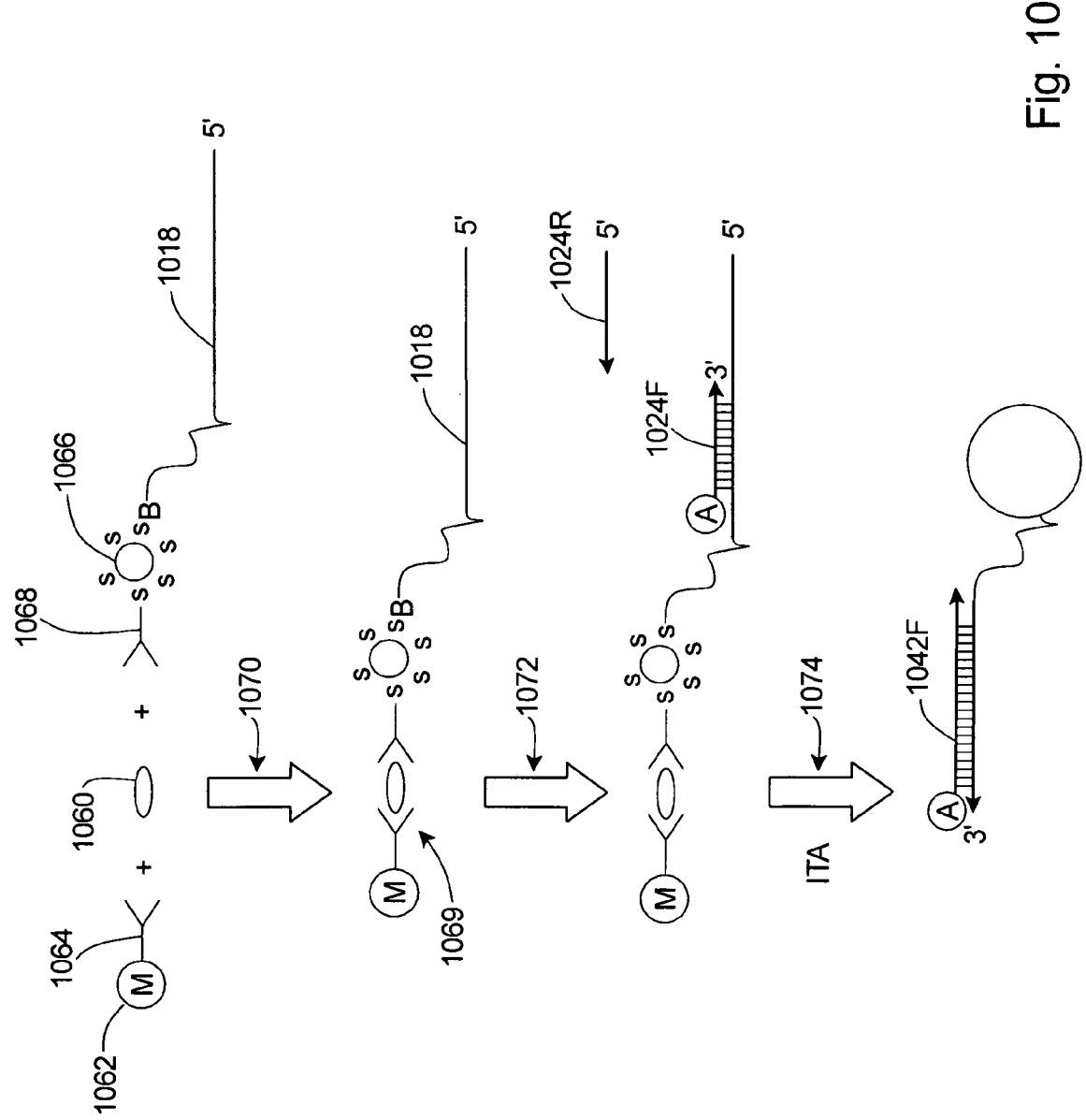
FIG. 10 is a workflow diagram showing an embodiment of a method including steps for amplification and detection of proteins in accordance with the present invention.

FIG. 10 is a workflow diagram showing an embodiment of a method including steps for amplification and detection of proteins in accordance with the present invention. In the embodiment illustrated in FIG. 10, an antibody sandwich assay is used to detect a spore 1060. A magnetic capture bead 1062 (illustrated with an "M" in a circle) containing a capture antibody 1064 is mixed together with a second non-magnetic "hybrid detection" bead 1066 which contains both one or more detection antibodies 1068 and one or more tails 1018. In another embodiment (not shown), the detection antibody 1068 can be directly linked to the tail 1018 instead of using the hybrid detection bead 1066 to link the detection antibody 1068 and the tail 1018.

The detection antibody 1068 on the hybrid detection bead 1066 recognizes a different epitope on the surface of the spore 1060. When spores 1060 are present in the reaction mixture, an antibody/spore compound 1069 is formed linking the hybrid detection bead 1066 to the magnetic capture bead 1060 via the spore 1060, at step 1070. Once this binding occurs over a sufficient time period, all unbound hybrid detection beads 1066 and any other unbound reactants are washed away at step 1072.

At step 1074, tappers 1024F, 1024R that are substantially similar to those described previously are added to the reaction mixture, including the antibody/spore compound 1069, along with the appropriate polymerase(s). Further, at this step, isothermal amplification occurs as previously described. Capture of the denatured reaction product, including the first strand 1042F and detection of those products can likewise occur as previously described herein, providing some or all of the advantages and benefits indicated above or inherently understood by those skilled in the art.

Figure 11:
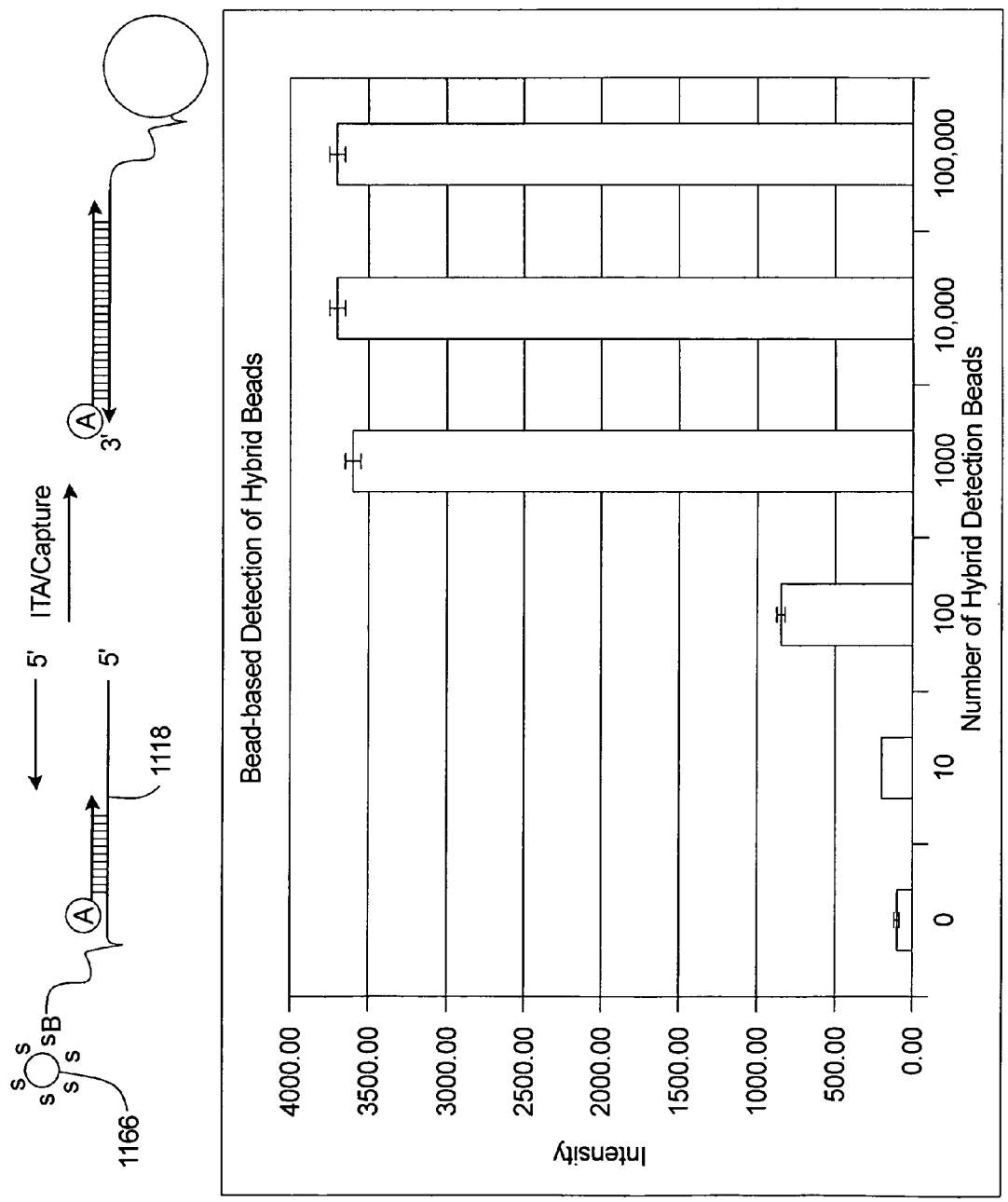
FIG. 11 is a workflow diagram and a graph illustrating detection results for hybrid detection beads.

FIG. 11 is a workflow diagram and a graph illustrating detection results for hybrid detection beads. In this experiment, isothermal amplification reactions were performed using different numbers of hybrid detection beads 1166 as templates. The isothermal amplification reactions resulted in detection of approximately 100 hybrid detection beads 1166 in less than five minutes, which is indicative of the speed and sensitivity of this approach for detecting proteins. The sensitivity of the approach is exemplified by the fact that each of the hybrid detection beads 1166 contains roughly 10,000 tails 1118.

While the particular methods and compositions for rapid amplification, capturing and/or detection of nucleic acid sequences and proteins as shown and disclosed herein are fully capable of obtaining the objects and providing the advantages herein before stated, it is to be understood that they are merely illustrative of the presently preferred embodiments of the invention and that no limitations are intended to the details of the methods, construction or design herein shown and described.

What is claimed is:

1. A method for detecting the presence of a nucleic acid template in a sample, the method comprising the steps of:
    combining the sample in a reaction vessel with a first primer and a second primer, the second primer including (i) a first section having a plurality of nucleotides that bind with a portion of the nucleic acid template, (ii) a second section that is spaced-apart from the first section, the second section including a plurality of nucleotides that do not bind with the nucleic acid template, and (iii) a spacer that couples the first section to the second section;
    extending the first section with additional nucleotides;
    binding the first primer to the extended first section;
    extending the first primer with additional nucleotides;
    terminating extension of the first primer with the spacer of the second primer;
    adding a forward tapper and a reverse tapper to the reaction vessel, the forward tapper binding to the second section and extending along the second section; and
    amplifying the second section to increase the number of second sections in the reaction vessel.

2. The method of claim 1 wherein the spacer is devoid of nucleotides.

3. The method of claim 1 wherein the second section includes at least approximately 5 nucleotides and less than approximately 50 nucleotides.

4. The method of claim 1 wherein the second section includes at least approximately 20 nucleotides and less than approximately 30 nucleotides.

5. The method of claim 1 wherein the second section includes a sequence of nucleotides that is non-complementary to the nucleic acid template.

6. The method of claim 1 wherein the step of combining includes including a tag sequence in the second section, the tag sequence being based on one or more criteria that are not dependent upon any sequence of nucleotides in the nucleic acid template.

7. The method of claim 6 wherein the tag sequence is specific to the nucleic acid template to be detected.

8. The method of claim 6 wherein the tag sequence is formed from at least 1 and less than approximately 5 nucleotides.

9. The method of claim 6 wherein the tag sequence is formed from approximately 4 nucleotides.

10. The method of claim 1 wherein the step of amplifying occurs substantially isothermally.

11. The method of claim 1 further comprising the step of including a tag sequence in the second section, the tag sequence being based on one or more criteria that are not dependent upon any sequence of nucleotides in the nucleic acid template, and wherein the step of the forward tapper binding includes the forward tapper binding to a portion of the second section that does not include the tag sequence.

12. The method of claim 1 wherein the step of combining includes adding a plurality of second primers, each of the second primers including a different second section, each second section being specific for detecting one particular nucleic acid template in the sample.

13. The method of claim 12 wherein the different second sections each has a different tag sequence that includes 1 to 5 nucleotides.

14. A method for detecting the presence of a nucleic acid template in a sample, the method comprising the steps of:
combining the sample in a reaction vessel with a first primer and a second primer, the second primer including (i) a first section having a plurality of nucleotides that bind with a portion of the nucleic acid template, (ii) a second section that is spaced-apart from the first section, the second section including a sequence of between 10 and 40 nucleotides, the sequence being non-complementary to the nucleic acid template, the second section being adapted to not bind with the nucleic acid template, the second section including a tag sequence of 2 to 4 nucleotides that are specific to the nucleic acid template being detected, and (iii) a spacer that couples the first section to the second section;
extending the first section with additional nucleotides;
binding the first primer to the extended first section;
extending the first primer with additional nucleotides;
terminating extension of the first primer with the spacer of the second primer;
adding a forward tapper and a reverse tapper to the reaction vessel, the forward tapper binding to the second section and extending along the second section; and
amplifying the second section to increase the number of second sections in the reaction vessel.

15. A method for detecting the presence of a nucleic acid template in a sample, the method comprising the steps of:
combining the sample in a reaction vessel with a first primer and a second primer, the second primer including (i) a first section having a plurality of nucleotides that bind with a portion of the nucleic acid template, (ii) a second section that is spaced-apart from the first section, the second section including a plurality of nucleotides that do not bind with the nucleic acid template, and (iii) a spacer that couples the first section to the second section, the spacer being devoid of nucleotides;
including a tag sequence in the second section, the tag sequence being based on one or more criteria that are not dependent upon any sequence of nucleotides in the nucleic acid template;
extending the first section with additional nucleotides;
binding the first primer to the extended first section;
extending the first primer with additional nucleotides;
terminating extension of the first primer with the spacer of the second primer;
adding a forward tapper and a reverse tapper to the reaction vessel, the forward tapper binding to the second section and extending along the second section; and
amplifying the second section to increase the number of second sections in the reaction vessel.

16. The method of claim 15 wherein the tag sequence is specific to the nucleic acid template to be detected.

17. The method of claim 15 wherein the tag sequence is formed from at least 1 and less than approximately 5 nucleotides.

18. The method of claim 15 wherein the tag sequence is formed from approximately 4 nucleotides.

19. The method of claim 14 wherein the spacer is devoid of nucleotides.

20. The method of claim 14 wherein the step of combining includes basing the tag sequence on one or more criteria that are not dependent upon any sequence of nucleotides in the nucleic acid template.

* * * * *